(12) United States Patent
Liu et al.

(10) Patent No.: US 8,283,463 B2
(45) Date of Patent: Oct. 9, 2012

(54) STERILE HYALURONIC ACID SOLUTIONS

(75) Inventors: X. Michael Liu, Pittsford, NY (US); David J. Heiler, Avon, NY (US); Thomas Menzel, Rochester, NY (US); Abbie Brongo, Victor, NY (US); Susan E. Burke, Batavia, NY (US); Karl Cummins, Hilton, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 328 days.

(21) Appl. No.: 12/702,540

(22) Filed: Feb. 9, 2010

(65) Prior Publication Data

US 2011/0195925 A1  Aug. 11, 2011

(51) Int. Cl.
*C07H 5/06* (2006.01)
*C08B 37/00* (2006.01)
(52) U.S. Cl. ............ 536/55.2; 536/55; 536/127; 514/54
(58) Field of Classification Search .................. None
See application file for complete search history.

(56) References Cited

U.S. PATENT DOCUMENTS

| | | | |
|---|---|---|---|
| 4,141,973 A | 2/1979 | Balazs | |
| 5,093,487 A | 3/1992 | Brown et al. | |
| 6,921,819 B2 * | 7/2005 | Piron et al. ................ | 536/55.3 |
| 7,105,473 B2 | 9/2006 | Glick et al. | |
| 2003/0176393 A1 * | 9/2003 | Koyama et al. ............. | 514/54 |
| 2006/0052336 A1 | 3/2006 | Carlino | |
| 2009/0036554 A1 * | 2/2009 | Burke et al. ................ | 514/779 |

FOREIGN PATENT DOCUMENTS

| | | |
|---|---|---|
| EP | 0867453 A2 | 9/1998 |
| EP | 0698388 B1 | 12/1999 |
| WO | WO 00/44925 A1 | 8/2000 |
| WO | WO 01/57172 A1 | 8/2001 |
| WO | WO 2004/014399 A1 | 2/2004 |
| WO | WO2009/063291 * | 5/2009 |

OTHER PUBLICATIONS

Blumberg et al., "Changes in the physical characteristics of the hyaluronate of ground substance with alterations in sodium chloride concentration," Columbia University College of Physicians and Surgeons, p. 1454-1461, (May 25, 1955).
Liu et al., "Detailed characterization of cationic hydroxyethylcellulose derivatives using aqueous size-exclusion chromatography with on-line triple detection," J of Chroma., 2006, vol. 1104, p. 145-153.

* cited by examiner

*Primary Examiner* — Eric S Olson
(74) *Attorney, Agent, or Firm* — Joseph Barrera (57) ABSTRACT

A process for sterilizing a solution comprising hyaluronic acid. The process comprises providing an aqueous solution of hyaluronic acid with a weight average molecular weight from 0.6 MDa to 3.6 MDa, and the concentration of the hyaluronic acid is from 0.04% to 0.8% by weight. The aqueous solution also has an ionic strength equivalent to an aqueous concentration of sodium chloride from 3% to 30% by weight. Once the aqueous, high salt, hyaluronic acid solution is prepared the solution is maintained at a temperature from 40° C. to 80° C. for at least 1 hour and not longer than six days. Following the heat treatment step, the aqueous solution is filtered through a sterilization filter medium to provide a sterilized high salt, hyaluronic acid solution.

21 Claims, 2 Drawing Sheets

STERILE HYALURONIC ACID SOLUTIONS

FIELD OF THE INVENTION

The invention is directed to filter sterilized, aqueous solutions that contain hyaluronic acid, and a process of preparing commercial volumes of sterile solutions comprising hyaluronic acid.

BACKGROUND OF THE INVENTION

Unfortunately, many biopolymers are sensitive to common sterilization procedures, e.g., heat sterilization. Heat sterilization can often lead to pronounced changes in the physicochemical properties of the biopolymer such that the resulting sterile biopolymer is rendered unsuitable for its intended use.

Sterilization methods that are currently applied to medical materials include, for example, heat treatment, high-pressure vapor sterilization (e.g. autoclave sterilization), ethylene oxide gas (EOG) sterilization, supercritical carbon dioxide sterilization and radiation sterilization. See for example, U.S. Pat. No. 6,891,035, U.S. Pat. No. 6,149,864, U.S. Pat. No. 5,621,093, U.S. Pat. No. 4,263,253, US 2006/0292030 and US 2007/0009578. Available sterilization methods are typically assessed in relation to the robustness of the particular biopolymer to be sterilized. For example, high-pressure vapor sterilization can be used for a biopolymer only to the extent that the biopolymer can endure high temperatures and high pressures. However, very few biopolymers including hyaluronic acid can endure such high temperatures and high pressures. EOG sterilization could be useful because the process suppresses the thermal breakdown of the biopolymer. However, the presence of residual ethylene oxide in the composition can be problematic.

Hyaluronic acid is a non-immunogenic substance and because of its viscoelastic and hydrophilic properties hyaluronic acid has been used for many years as an eye vitreous or joint fluid replacement or as a supportive medium in ophthalmic surgery, as disclosed for example in U.S. Pat. No. 4,141,973 of Balazs. In joint fluids, the hyaluronic acid solution serves as a lubricant to provide a protective environment to the cells, and for this reason, it is used in the treatment of inflamed knee joints. EP-A-0 698 388 of Chemedica S. A. discloses an ophthalmic preparation for use as artificial tears containing hyaluronate as a viscosity thickener. The consumer use of products that include hyaluronic acid requires the manufacturer to sterilize the consumer product, and if used as an open multi-dose formulation, an additional step must be taken to preserve the formulation product.

Hyaluronic acid is one biopolymer known to be very sensitive to thermal sterilization processes. Heat sterilization of hyaluronic acid is known to accelerate the hydrolysis or oxidation of hyaluronic acid, thereby causing a significant and often detrimental decrease in the average molecular weight of the biopolymer. For many pharmaceutical applications, a relatively low molecular weight form of hyaluronic acid in the formulation is not desirable. Typically, the low molecular weight forms of hyaluronic acid do not provide the desired rheological properties of the high molecular weight form of hyaluronic acid. To compensate for the breakdown of the hyaluronic acid in the aforementioned heat sterilization methods, one could possibly begin with a hyaluronic acid with a higher molecular weight than desired. This accommodation, however, leads to process inefficiencies because the product yield of hyaluronic acid decreases as the average molecular weight of the biopolymer increases.

Another known method of sterilizing hyaluronic acid is by filtration. Common filtration processes are used in industrial processes for preparing purified hyaluronic acid salts in a concentrated form, usually in the form of dried powder, whereby an aqueous solution is passed through the filter and subsequently dried. Such a filtration processes is described in European patent application EP 867453 and WO 00/44925. U.S. Publication No. 2006/0052336 describes a method of filter sterilizing a high molecular weight hyaluronic acid at a relatively low hyaluronic acid concentration to reduce the viscosity of the solution. Following the filtration step, the concentration of the hyaluronic acid in the solution is concentrated by applying a vacuum and removing the water to obtain a desired more concentrated form of hyaluronic acid.

U.S. Pat. No. 5,093,487 describes a method of preparing an aqueous solution containing a high molecular weight form of hyaluronic acid (preferably greater than 1.2 MDa) that can be filtered more easily by reducing the viscosity of the solution. This reduction in viscosity of the solution is said to be possible by a "controlled heat treatment" or by "filtration of a minimum concentration solution with high pressure or vacuum through small pore membranes." These viscosity reducing processes also lead to a hyaluronic acid form that maintains its lower viscosity over time, i.e., the induced reduction in viscosity is stated as being irreversible. In particular, the heat treatment of a 1 wt. % hyaluronic acid solution having an initial weight average molecular weight of 1.1 MDa at different heating temperatures (30° C., 40° C. and 50° C.) over a one month treatment period is described. For each hyaluronic acid solution no reduction of the weight average molecular weight is reported. The '487 patent also reports that the heat treated solutions of hyaluronic acid can be filtered through a 0.22 micron pore size filter required for sterilization.

Blumberg et al., in *Changes in Physical Characteristics of Hyaluronate*, pp. 1454-61, reports on changes in the physical characteristics of hyaluronic acid solutions as a function of sodium chloride concentration. With respect to viscosity, an increase in the ionic strength of the solution results in a decrease in viscosity. The decrease in viscosity is observed upon the addition of relatively small amounts of salt. "After approximately 0.5 M [NaCl], the drop [in viscosity] is gradual and after 1.3 M, there is very little change with the addition of even large amounts of salt." Id. at 1456. In other words, the viscosity is very sensitive to changes in sodium ion concentration just below that of physiological saline, and beyond a "sodium ion strength of approximately 0.15, the hyaluronate is relatively insensitive." Id. at 1459.

Based upon the foregoing, it can be seen that the sterilization of aqueous biopolymer solutions, and in particular, aqueous solutions of hyaluronic acid, is not at all routine, and there are numerous technical challenges to arrive at a substantially non-degraded sterile solution. These technical challenges are magnified if a commercial-scale production batch is the objective.

SUMMARY OF THE INVENTION

The invention is directed to a process for sterilizing a solution comprising hyaluronic acid. The process comprises providing an aqueous solution of hyaluronic acid with a weight average molecular weight from 0.6 MDa to 3.6 MDa, and the concentration of the hyaluronic acid is from 0.04% to 0.8% by weight. The aqueous solution also has an ionic strength equivalent to an aqueous concentration of sodium chloride from 3% to 30% by weight. Once the aqueous, high salt, hyaluronic acid solution is prepared the solution is maintained at a temperature from 40° C. to 80° C. for at least 1 hour and not longer than six days. Following the heat treatment step, the aqueous solution is filtered through a sterilization filter medium to provide a sterilized high salt, hyaluronic acid solution.

In one embodiment, the process comprises providing an aqueous solution of hyaluronic acid with a weight average molecular weight from 0.8 MDa to 2.2 MDa, and the concentration of the hyaluronic acid is from 0.1% to 0.5% by weight. The aqueous solution also has an ionic strength equivalent to an aqueous concentration of sodium chloride from 4% to 18% by weight. Once the aqueous, high salt, hyaluronic acid solution is prepared the solution is maintained at a temperature from 50° C. to 75° C. for at least 1 hour and not longer than 18 hours. Following the heat treatment step, the aqueous solution is filtered through a sterilization filter medium as described.

The invention is also directed to an aqueous solution comprising 0.04% to 0.8% by weight hyaluronic acid with a weight average molecular weight from 0.6 MDa to 3.6 MDa. The aqueous hyaluronic acid solution also comprises 4% to 18% by weight of sodium chloride, and the solution is filter sterilized.

The invention is also directed to an aqueous high salt, hyaluronic acid solution comprising an ionic strength equivalent of approximately 25 g to 60 g of sodium chloride for every 1 g of hyaluronic acid in one liter of solution. The concentration of hyaluronic acid in the solution is from 0.05% to 0.4% by weight.

DETAILED DESCRIPTION OF THE INVENTION

A "sterile" composition is one that is free of viable microbes as determined using the USP sterility test. See "The United States Pharmacopeia", 30th Revision, The United States Pharmacopeial Convention: 2008.

The term "hyaluronic acid" refers to a polymer comprising repeat disaccharide subunits of hyaluronan. The term also includes a polymer in which the disaccharide subunits may be derivatized at one or more positions of the D-glucuronic acid and/or the D-N-acetylglucosamine repeat subunit. Accordingly the term hyaluronic acid encompasses hyaluronic acid, derivatized forms of hyaluronic acid, and salts forms (also referred to as hyaluronate, e.g., sodium hyaluronate).

Hyaluronic acid is a linear polysaccharide (long-chain biological polymer) formed by repeating disaccharide units consisting of D-glucuronic acid and N-acetyl-D-glucosamine linked by $\beta(1\text{-}3)$ and $\beta(1\text{-}4)$ glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is well accepted by the ophthalmic community as a compound that can protect biological tissues or cells from compressive forces. Accordingly, hyaluronic acid has been proposed as a component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

Hyaluronic acid solutions are known to be sensitive to heat and acid hydrolysis, and thus, the weight average molecular weight will typically decrease over time if the solutions are subjected to conditions that facilitate the hydrolysis of the polysaccharide linkage. In the case of aqueous solutions of hyaluronic acid, prolonged heating above 80° C., e.g., conditions used to heat sterilize, is not suitable—substantial reduction in the weight average molecular weight of the hyaluronic acid is observed. Also, the use of a 0.22 micron pore size filter to sterilize aqueous hyaluronic acid solutions with a relatively high weight average molecular weight hyaluronic acid is not suitable—the smaller molecular weight fractions easily pass through the filter whereas the large fractions (avg. MW of about 0.6 MDa or greater) having an average molecular diameter greater than 0.2 μm do not. Applicants, however, have discovered select processing conditions that facilitate the filter sterilization of aqueous solutions of hyaluronic acid with a weight average molecular weight from 0.6 MDa to 3.6 MDa.

The described processing conditions improve upon the filtration efficiency of aqueous hyaluronic acid solutions. In particular, the described processing conditions make possible the sterilization of relatively large scale, production batches of aqueous hyaluronic acid solutions. Applicants demonstrate that a sterile filtration of an aqueous solution that contains hyaluronic acid with a weight average molecular weight from 0.6 MDa to 3.6 MDa and a concentration of hyaluronic acid from 0.04% to 0.8% by weight can be filtered through a 0.22 micron pore size filter, and thus, sterilized in large scale, commercial production batches. The described process essentially relies upon a specified heat treatment of the solution and the solution having a relatively high ionic strength.

One process condition involves a heat treatment. In this case, the aqueous hyaluronic acid solution is maintained at a temperature from 40° C. to 80° C. for at least 1 hour and not longer than six days. One must be careful, however, not to maintain the temperature of the solution at the high end of this temperature range for a period longer than 24 hours, otherwise one begins to observe a significant decrease in the weight average molecular weight of the hyaluronic acid. Maintaining the temperature at or above 80° C. for an extended period of time can lead to hydrolytic or oxidative degradation of the polysaccharide linkage. Given the correlation between the duration of heat treatment and maintenance temperature with respect to minimizing an observed decrease in the weight average molecular weight of the hyaluronic acid recommended heat treatments are listed in Table 1 for hyaluronic acid with a weight average molecular weight of about 0.6 MDa to 1.6 MDa. Likewise, recommended heat treatments are listed in Table 2 for hyaluronic acid with a weight average molecular weight of about 1.6 MDa to 3.6 MDa.

TABLE 1

Heat Treatments for 0.6 to 1.6 MDa Hyaluronic Acid

| time (hr) | Temp. ° C. |
|---|---|
| 1-4 | 75 |
| 2-6 | 70 |
| 2-8 | 65 |
| 3-12 | 60 |
| 4-24 | 55 |
| 7-48 | 50 |
| 12-96 | 45 |

TABLE 2

Heat Treatments for 1.6 to 3.6 MDa Hyaluronic Acid

| time (hr) | Temp. ° C. |
|---|---|
| 2-6 | 75 |
| 3-8 | 70 |
| 3-10 | 65 |
| 6-16 | 60 |
| 6-24 | 55 |
| 10-48 | 50 |
| 14-140 | 45 |

Figure 2:
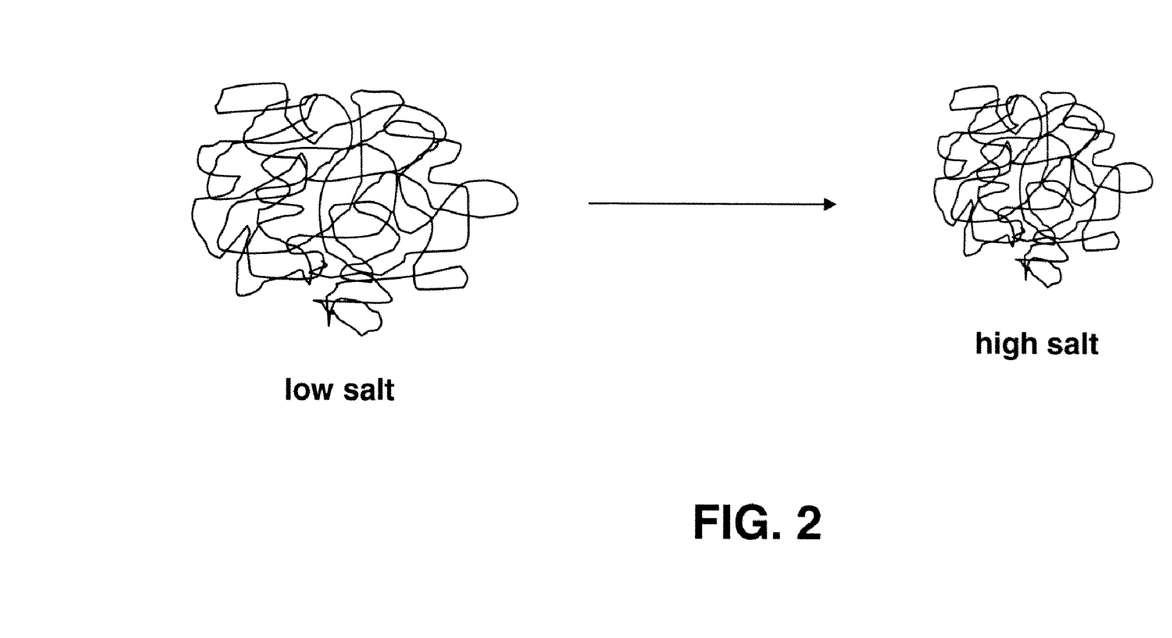
FIG. 2 shows a schematic representation of a random coiled, hyaluronic acid polymer in aqueous solution with different ionic strength (ionic salt concentrations).

A second process condition involves the ionic strength of the aqueous hyaluronic acid solution. The ionic strength values are stated and described as an equivalent to a stated aqueous concentration of sodium chloride. Applicants at times refer to the increase in ionic strength of the aqueous hyaluronic acid solutions as a "salt shrink wrapping" of the polymer. The "salt shrink wrapping" of the hyaluronic acid is best described by the schematic representation of a random coiled, hyaluronic acid in aqueous solution shown in FIG. 2.

Accordingly, a sufficient amount of one or more salt compounds are combined with the hyaluronic acid to provide an aqueous high salt, hyaluronic acid solution having an ionic strength equivalent to an aqueous concentration of sodium chloride of from 3 wt. % to 30 wt. %, from 4 wt % to 18 wt. %, or from 8 wt. % to 14 wt. %.

Ideally, the one or more salts used to increase the ionic strength of the aqueous hyaluronic acid solution is a salt that is to be present in a desired product formulation. For example, if it is necessary to buffer the formulation, one of the salts can be the salt component of the buffer. In the case of a borate buffered, formulation the salt can be an alkali borate salt, e.g., sodium borate. Likewise, in the case of a citrate or phosphate buffered, formulation the salt can be an alkali citrate salt, e.g., sodium citrate, or an alkali phosphate salt, e.g., disodium phosphate, respectively. One of ordinary skill in the art would understand that any salt buffer component can be used to increase the ionic strength of the aqueous hyaluronic acid solution.

In the case of preparing ophthalmic preparations, alkali metal chlorides such as NaCl or KCl are typically used to control the osmolality of the preparation. Accordingly, NaCl, KCl or some combination of the two salts can be used to increase the ionic strength of the aqueous hyaluronic acid solution. Alternatively, other common salts can be used including Group II metal salts, e.g. magnesium or calcium chloride.

In one embodiment, a high salt, hyaluronic acid solution will have an ionic strength equivalent of approximately 25 g to 60 g of sodium chloride for every one gram of hyaluronic acid in a one liter solution. For example, a 0.1 wt. % hyaluronic acid solution will include an ionic strength equivalent of approximately 25 g to 60 g of sodium chloride. Likewise, a 0.2 wt. % hyaluronic acid solution will include an ionic strength equivalent of approximately 50 g to 120 g of sodium chloride. A 0.3 wt. % hyaluronic acid solution will include an ionic strength equivalent of approximately 75 g to 180 g of sodium chloride.

Optional Addition of an Acid

The pH of the solution is also observed to have an impact on the efficiency of passing an aqueous hyaluronic acid solution through a sterilizing filter medium with a 0.22 micron pore size. The pH of the solution can also have an impact on the rate of hydrolysis of the hyaluronic acid at temperatures used in the heat treatment step. A reduction of the pH to a value of about 4.2 to about 6.2, preferably a pH value of about 5.2 to about 6.2, can also facilitate the sterile filtration process of a hyaluronic acid solution. Typically, one would add a buffering acid associated with the buffer salt that is present in the final formulation product. For example, if it is necessary to buffer the formulation, one would use the corresponding free acid. In the case of a borate buffered, formulation one would likely add boric acid. Likewise, in the case of a citrate buffered, formulation, one would likely add citric acid.

There is, however, a tradeoff if one was to prepare an aqueous hyaluronic acid solution with a pH value less than about 6.4 that is then to be filter sterilized using the described process. As stated, aqueous solutions of hyaluronic acid are sensitive to hydrolysis, i.e., the hydrolytic cleavage of a polysaccharide linkage, which leads to an undesired decrease in the weight average molecular weight of the hyaluronic acid. Applicants believe that the hydrolysis reaction is catalyzed by the presence of acid, and thus, a lower pH value will often correspond to an increase rate of hydrolysis. Therefore, one in the art is faced with two competing factors and must decide on process conditions that optimize a sterile filtration process for a select grade of hyaluronic acid. A lower pH value of the solution results in a decrease in viscosity of the solution, and thus, a higher flow rate through the sterilization filter. At the same time, a lower pH value can lead to an increase rate in hydrolysis and a hyaluronic acid with a lower weight average molecular weight.

Similarly, the rate of hydrolysis hyaluronic acid is also accelerated under relatively high basic conditions, e.g., a pH value of at least 7.8 or higher. Accordingly, the preferred salts added to prepare the high salt, hyaluronic acid solution is a neutral salt, e.g., a Group I or Group II metal chloride. The preferred pH range for the described sterile filtration of hyaluronic acid is from about 6.4 to about 7.2.

Applicants investigated two types of sterilizing filter mediums having a pore size of 0.22 microns to filter the hyaluronic acid solutions; a bilayer polyethersulfone (PES) medium and a hydrophobic polyvinylidene fluoride (PVDF) medium. Both filter mediums worked quite well on a laboratory scale, however, in a commercial process environment the larger PVDF cartridges provided more consistent flow rates from batch to batch.

Figure 1:
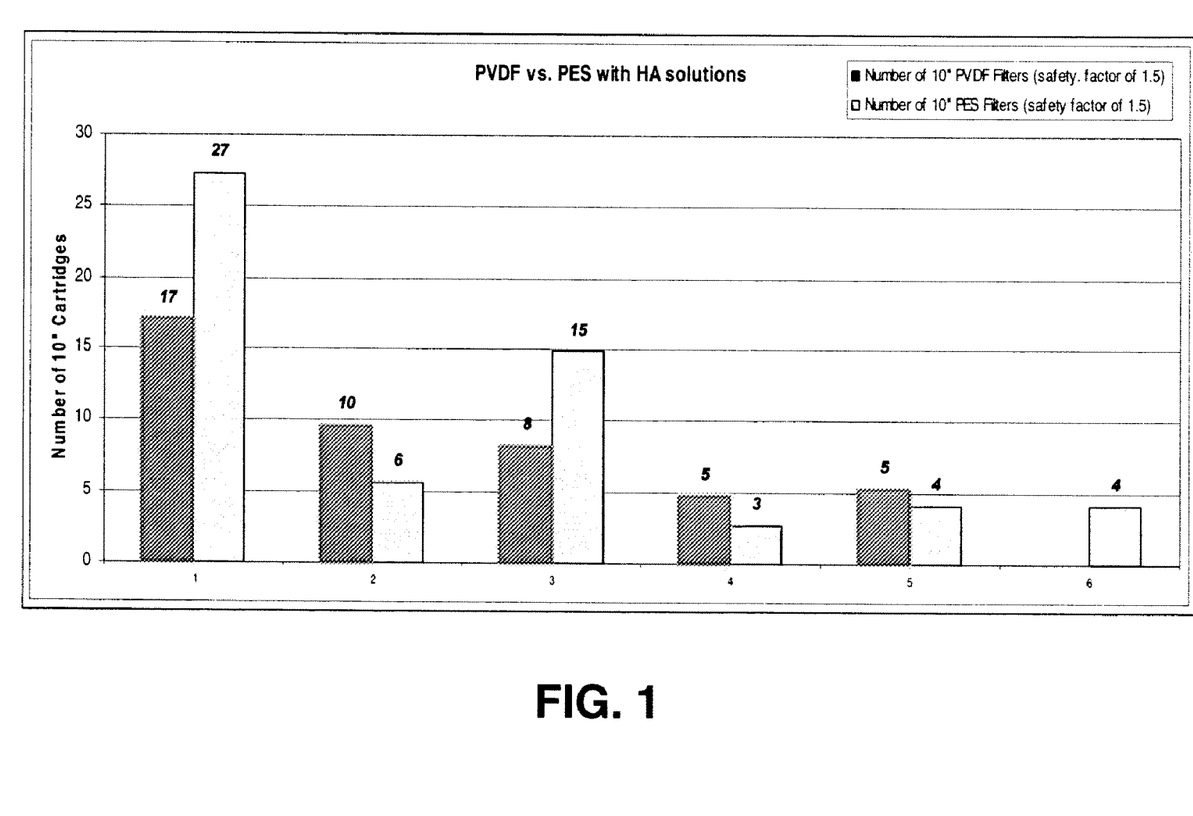
FIG. 1 is a bar graph representation that shows the estimated number of 10-inch filter cartridges that would be required to process approximately 740 kg of aqueous hyaluronic acid solution for the various process conditions listed.

FIG. 1 is a bar graph that shows the estimated number of 10-inch filter cartridges that would be required to process approximately 740 kg of aqueous hyaluronic acid solution for various process conditions. The actual studies were conducted with about 2 L of hyaluronic acid solution using a 47 mm filter disc. The variables in these studies included: the concentration of the hyaluronic acid; the ionic strength of the solution as reported by the concentration of sodium chloride in the solution; the filter mediums used (PES or PVDF); and the absence or presence of boric acid in the solution. Applicants attempted to keep the weight average molecular weight hyaluronic acid as consistent as possible across the study runs, however, there was a slight variation in the weight average molecular weight of the hyaluronic acid in the study lots. The molecular weights and molecular weight distributions of sodium hyaluronate are determined by aqueous size exclusion chromatography with on-line triple detection. See, Liu, X. M. et al. *Detailed Characterization of Cationic Hydroxyethylcellulose Derivatives using Aqueous Size-Exclusion Chromatography with on-line Triple Detection.* J. Chromatogr. A. 1104, 2006. 145-153.

As would be understood by one of skill in the art, the described sterile filtration process is limited by the viscosity of the aqueous high salt hyaluronic acid solution. Accordingly, the concentration of the hyaluronic acid in the high salt hyaluronic acid solution is less than 0.8 wt. % as any further increase in concentration of the hyaluronic acid would render the solution to viscous to filter even a heat treated, high salt solution. Again, heating the solutions beyond 80° C. for a time sufficient to filter sterilize higher concentrations of hyaluronic acid would likely lead to significant thermal hydrolysis of the polysaccharide linkages resulting in a significant decrease in the weight average molecular weight and likely to a loss in the beneficial viscoelastic properties originally sought for the desired product formulation.

In many embodiments, the concentration of the hyaluronic acid in the high salt hyaluronic acid solution is from 0.04 wt. % to 0.8 wt. % or from 0.1 wt. % to 0.4 wt. %, e.g., about 0.2 wt. %, about 0.3 wt. %, about 0.4 wt. %, or about 0.5 wt. %.

EXAMPLE 1

FIG. 1. A 0.5 wt. % hyaluronic acid (HA) was prepared by slowly adding a dry blended mixture of 10.0 g HA and 250 g NaCl (12.5 wt. %) to 1740.0 g of purified water maintained at about 70° C. in a stainless container with agitation. The HA had a reported weight average molecular weight of about 1.8 MDa. The HA appeared fully dissolved after about 20 min. The solution was allowed to cool to room temperature and stored in two plastic bottles. The solution had a cone/plate viscosity of 304 cP at 1 rpm, 111 cP at 17 rpm.

Solution A. [comp. ex. A] A 0.5 wt. % hyaluronic acid (HA) was prepared by slowly adding 10.0 g HA to 1990.0 g of purified water maintained at about 70° C. in a stainless container with agitation. The HA appeared fully dissolved after about 47 min. The solution was allowed to cool to room temperature and stored in two plastic bottles. The solution had a cone/plate viscosity of 1343 cP at 1 rpm, 192.2 cP at 17 rpm.

Solution B. [comp. ex. B] A 1.0 wt. % hyaluronic acid (HA) was prepared by slowly adding 20.0 g HA to 1980.0 g of purified water maintained at about 70° C. in a stainless container with agitation. The HA appeared fully dissolved after about 75 min. The solution was allowed to cool to room temperature and stored in two plastic bottles. Due to the apparent high viscosity of the solution a viscosity measurement was not obtained.

Solution C. [comp. ex. C] A 3.0 wt. % hyaluronic acid (HA) was prepared by slowly adding 15.0 g HA to 485.0 g of purified water maintained at about 70° C. in a stainless container with agitation. The HA appeared fully dissolved after about 150 min. The product resulted in the formation of a very thick, non-pourable gel and actually began to move up the stirring shaft. A viscosity measurement was not obtained.

In one embodiment, the described sterile filtration process includes the following process and solution conditions for either a 0.22 micron pore size PES or PVDF filter cartridge. A hyaluronic acid with a weight average molecular weight of from about 0.7 MDa to about 1.7 MDa is commercially obtained as a fine dry powder. An appropriate amount of the dry hyaluronic acid is added to a dry blending vessel along with an appropriate amount of sodium chloride. The two powders are dry blended effectively diluting the hyaluronic acid in the sodium chloride. Meanwhile purified water is added to a mixing tank and the temperature of the water is heated to and maintained from 40° C. to 80° C. The dry blended hyaluronate/NaCl is slowly added to the purified water and the solution agitated until the hyaluronic acid visibly appears to be completely in solution (i.e., dissolved). The high salt hyaluronic acid solution is then heat treated at a temperature from 40° C. to 80° C. for at least one hour and not longer than six days. Again, it is to be understood that the higher the maintenance temperature the shorter the duration of the heat treatment. Following the heat treatment the high salt hyaluronic acid solution is preferably cooled to about 45° C. to 55° C. if, of course, the maintenance temperature is greater than 55° C.

In many embodiments, the hyaluronic acid will have a weight average molecular weight from 0.6 MDa to 3.6 MDa, from 0.8 MDa to 2.2 MDa, from 0.8 MDa to 1.6 MDa or from 1.1 MDa to 1.4 MDa.

EXAMPLE 2

FIG. 1. A 0.25 wt. % hyaluronic acid (HA) was prepared by slowly adding a dry blended mixture of 10.0 g HA and 500 g NaCl (12.5 wt. %) to 3490.0 g of purified water maintained at about 78° C. in a stainless container with agitation. The HA had a reported weight average molecular weight of about 1.8 MDa. The solution was allowed to cool to room temperature. The solution had a cone/plate viscosity of 16.3 cP at 30 rpm.

EXAMPLE 3

FIG. 1. A 0.125 wt. % hyaluronic acid (HA) was prepared by slowly adding a dry blended mixture of 5.0 g HA and 250 g NaCl (6.25 wt. %) to 3745.0 g of purified water maintained at about 73° C. in a stainless container with agitation. The HA had a reported weight average molecular weight of about 1.4 MDa. The HA appeared fully dissolved after about 75 min. The solution was allowed to cool to room temperature. The solution had a cone/plate viscosity of 6.4 cP at 60 rpm.

EXAMPLE 4

FIG. 1. A 0.125 wt. % hyaluronic acid (HA) was prepared by slowly adding a dry blended mixture of 5.0 g HA and 250 g NaCl (6.25 wt. %) to 3485.0 g of purified water maintained containing 160 g boric acid (4 wt. %) at about 76° C. in a stainless container with agitation. The HA had a reported weight average molecular weight of about 1.4 MDa. The solution was allowed to cool to room temperature. The solution had a cone/plate viscosity of 3.5 cP at 60 rpm.

As suggested by the data reported in FIG. 1, the solution of Example 4 with 4 wt. % boric acid is nearly two-times more efficient passing through a PVDF filter disc than a comparable solution without the boric acid, i.e., the solution of Example 3. Moreover, the solution of Example 4 is five-times more efficient passing through a PES filter disc than the solution of Example 3.

EXAMPLE 5

FIG. 1. A 0.25 wt. % hyaluronic acid (HA) was prepared by slowly adding a dry blended mixture of 5.0 g HA and 250 g NaCl (12.5 wt. %) to 1745.0 g of purified water maintained at about 75° C. in a stainless container with agitation. The HA had a reported weight average molecular weight of about 0.8 MDa. The HA appeared fully dissolved after about 30 min. The solution was allowed to cool to room temperature. The solution had a cone/plate viscosity of 8.3 cP at 60 rpm.

EXAMPLE 6

FIG. 1. A 0.25 wt. % hyaluronic acid (HA) was prepared by slowly adding a dry blended mixture of 4.0 g HA and 200 g NaCl (12.5 wt. %) to 1396.0 g of purified water maintained at about 73° C. in a stainless container with agitation. The HA had a reported weight average molecular weight of about 0.7 MDa. The HA appeared fully dissolved after about 30 min. The solution was allowed to cool to room temperature. The solution had a cone/plate viscosity of 8.7 cP at 60 rpm.

Effect of Maintenance Temperature on Molecular Weight

EXAMPLE 7A

A high salt, hyaluronic acid solution was prepared containing 0.26 wt. % hyaluronic acid and 13 wt. % NaCl as described in Example 2. A dry blended mixture of 5.2 g HA and 260 g NaCl was slowly added to 1734.8 g of heat distilled water maintained at 69° C. in a stainless container with agitation. The HA appeared fully dissolved after about 105 min at which time the temperature was 66° C. The solution was cooled to about 40° C. in about 10 min and maintained at about 40° C. Samples were withdrawn at 0 hr, 1 hr, 2 hr, 3 hr, 4 hr and 18 hr during which time the temperature of the solution varied from 38° C. (18 hr) to 44° C. (4 hr). An aqueous GPC-triple detection system was used to determine the weight average molecular weight of each sample. Cone/plate viscosity determinations were also made for each sample at 12 rpm. Both the GPC molecular weight data and viscosity data is listed in Table 3.

TABLE 3

Ex. 7A Data 40° C.

| time (hr) | $M_w \cdot 10^3$ | viscosity cP |
| --- | --- | --- |
| 0 | 1475 | 22.6 |
| 1 | 1463 | 22.3 |
| 2 | 1475 | 21.9 |
| 3 | 1455 | 21.8 |
| 4 | 1459 | 21.6 |
| 18 | 1463 | 20.1 |

EXAMPLE 7B

A high salt, hyaluronic acid solution was prepared containing 0.26 wt. % hyaluronic acid and 13 wt. % NaCl as described in Example 2. A dry blended mixture of 5.2 g HA and 260 g NaCl was slowly added to 1734.8 g of heat distilled water maintained at 67° C. in a stainless container with agitation. The HA appeared fully dissolved after about 115 min at which time the temperature was 69° C. The solution was cooled to about 50° C. in about 10 min and maintained at about 50° C. Samples were withdrawn at 0 hr, 1 hr, 2 hr, 3 hr, 4 hr and 18 hr during which time the temperature of the solution varied from 46° C. (18 hr) to 54° C. (3 hr). An aqueous GPC-triple detection system (Integrated PL-GPC50 with 2× Waters Ultrahydrogel Linear, 7.8×300 mm) was used to determine the weight average molecular weight of each sample. Cone/plate viscosity determinations were also made for each sample at 12 rpm. Both the GPC molecular weight data and viscosity data is listed in Table 4.

TABLE 4

Ex. 7B Data 50° C.

| time (hr) | $M_w \cdot 10^3$ | viscosity cP |
| --- | --- | --- |
| 0 | 1506 | 29.5 |
| 1 | 1511 | 29.0 |
| 2 | 1474 | 28.9 |
| 3 | 1488 | 28.6 |
| 4 | 1507 | 27.7 |
| 18 | 1462 | 24.7 |

EXAMPLE 7C

A high salt, hyaluronic acid solution was prepared containing 0.26 wt. % hyaluronic acid and 13 wt. % NaCl as described in Example 2. A dry blended mixture of 5.2 g HA and 260 g NaCl was slowly added to 1734.8 g of heat distilled water maintained at 70° C. in a stainless container with agitation. The HA appeared fully dissolved after about 125 min at which time the temperature was 67° C. The solution was cooled to about 61° C. in about 5 min and maintained at about 60° C. Samples were withdrawn at 0 hr, 1 hr, 2 hr, 3 hr, 4 hr and 18 hr during which time the temperature of the solution varied from 56° C. (18 hr) to 61° C. (0 hr). An aqueous GPC-triple detection system was used to determine the weight average molecular weight of each sample. Cone/plate viscosity determinations were also made for each sample at 30 rpm. Both the GPC molecular weight data and viscosity data is listed in Table 5.

TABLE 5

Ex. 7C Data 60° C.

| time (hr) | $M_w \cdot 10^3$ | viscosity cP |
| --- | --- | --- |
| 0 | 1389 | 16.0 |
| 1 | 1326 | 14.8 |
| 2 | 1327 | 13.9 |
| 3 | 1305 | 13.0 |
| 4 | 1328 | 12.2 |
| 18 | 1174 | 9.7 |

EXAMPLES 8A to 8C

Example 7 was repeated with the exception that a second lot of hyaluronic acid was used and the maintenance temperature were about 50° C. (8A), 55° C. (8B) and 60° C. (8C). Molecular weight determinations are listed in Table 6.

TABLE 6

| time (hr) | $M_w \cdot 10^3$ 8A | $M_w \cdot 10^3$ 8B | $M_w \cdot 10^3$ 8C |
| --- | --- | --- | --- |
| 0 | 1666 | 1537 | 1173 |
| 1 | 1654 | 1513 | 1094 |
| 2 | 1605 | 1515 | 1024 |
| 3 | 1619 | 1472 | 1020 |
| 4 | 1607 | 1467 | 918 |
| 19 | 1546 | 1373 | 805 |

EXAMPLE 9

A high salt, hyaluronic acid solution was prepared containing 0.26 wt. % hyaluronic acid and 13 wt. % NaCl. A dry blended mixture of 5.2 g HA and 260 g NaCl was slowly added over 5 min to 1734.8 g of heat distilled water maintained at about 66° C. in a stainless container with agitation. The HA appeared fully dissolved after about 107 min at which time the temperature was about 70° C. The solution was cooled to about 50° C. in about 5 min and maintained at about 50° C. A Vmax 47 mm disc filter (STW 0.2 Everlux™ 0.45/0.22 micron) was pre-flushed with water at 50° C. for 5 min. The heat treated, high salt, hyaluronic acid solution was filtered through the filter at 27 psi. Using a Millipore conversion program the disc filtration would require about 2.7 10-inch filter cartridges for a 777 L solution volume.

EXAMPLE 10

A similar experiment to Example 9 with the exception that the HA and NaCl concentrations were reduced by 25%. A high salt, hyaluronic acid solution was prepared containing 0.195 wt. % hyaluronic acid and 9.75 wt. % NaCl. A dry blended mixture of 3.9 g HA and 195 g NaCl was slowly added over 5 min to 1801.1 g of heat distilled water maintained at about 69° C. in a stainless container with agitation. The HA appeared fully dissolved after about 100 min at which time the temperature was about 69° C. The solution was cooled to about 51° C. in about 7 min and maintained at about 51° C. A Vmax 47 mm disc filter (STW 0.2 Everlux™ 0.45/0.22 micron) was pre-flushed with water at 50° C. for 5 min. The heat treated, high salt, hyaluronic acid solution was filtered through the filter at 27 psi. Using a Millipore conversion program the disc filtration would require about 2.6 10-inch filter cartridges for a 777 L solution volume.

EXAMPLE 11

A similar experiment to Example 9 with the exception that the HA and NaCl concentrations were reduced by 50%. A high salt, hyaluronic acid solution was prepared containing 0.13 wt. % hyaluronic acid and 6.5 wt. % NaCl. A dry blended mixture of 2.6 g HA and 130 g NaCl was slowly added over 5 min to 1867.4 g of heat distilled water maintained at about 68° C. in a stainless container with agitation. The HA appeared fully dissolved after about 97 min at which time the temperature was about 69° C. The solution was cooled to about 49° C. in about 8 min and maintained at about 49° C. A Vmax 47 mm disc filter (STW 0.2 Everlux™ 0.45/0.22 micron) was pre-flushed with water at 50° C. for 5 min. The heat treated, high salt, hyaluronic acid solution was filtered through the filter at 27 psi. Using a Millipore conversion program the disc filtration would require about 3.0 10-inch filter cartridges for a 777 L solution volume.

In one embodiment, a process for sterilizing an aqueous hyaluronic acid solution with an appropriate filter medium is described. The process comprises providing an aqueous solution of hyaluronic acid having a weight average molecular weight from 0.6 MDa to 3.6 MDa. The concentration of the hyaluronic acid in the solution is from 0.04% to 0.8% by weight. Also, to facilitate the filtration efficiency the aqueous solution has an ionic strength equivalent to an aqueous concentration of sodium chloride from 3% to 30% by weight. The presence of the salt reduces the solution viscosity of the hyaluronic acid solution. Applicants believe that the hyaluronic acid is more tightly wrapped in a relatively high ionic strength solution resulting in a reduced radius of gyration of the biopolymer. The high salt, hyaluronic acid solution is subjected to a heat treatment, which further reduces the viscosity of the solution. Accordingly, the high salt, hyaluronic acid solution is maintained at a temperature from 40° C. to 80° C. for at least 1 hour and not longer than six days. The heat treated solution is then filtered through a sterilization filter medium. The filter medium has an average pore size of 0.25 μm or less, e.g., a 0.22 μm pore size, to provide a sterilized high salt, hyaluronic acid solution. To facilitate the dissolution of the hyaluronic acid upon its addition to the water (typically, the hyaluronic acid is commercially available as a fine dry powder), the hyaluronic acid is preferably dry blended with the salt, e.g., NaCl. The dry blended salt/hyaluronic acid mixture is then slowly added to an appropriate amount of purified water with agitation.

In one embodiment, the heat treatment of the high salt, hyaluronic acid solution involves maintaining the solution at a temperature from 40° C. to 70° C., though generally, the solution is maintained at a temperature from 50° C. to 70° C. for 1 hour to 12 hours. Again, with a higher the maintenance temperature shorter maintenance times are needed. For example, if the aqueous high salt, hyaluronic acid solution aqueous high salt is maintained at a temperature from 55° C. to 65° C., a maintenance time of at least 1 hour and not longer that 12 hours is recommended under such a heat treatment.

The sterilized high salt, hyaluronic acid solution preferably has a concentration of the hyaluronic acid from 0.15% to 0.6% by weight, and a preferred ionic strength equivalent to an aqueous concentration of sodium chloride from 4% to 16% by weight.

As stated, pH can play a role in the rate of hydrolysis of the hyaluronic acid polymer, which is believed to be catalyzed in the presence of acid or base. Accordingly, the high salt, hyaluronic acid solution is best prepared at a pH of 6.4 to 7.2 to limit the hydrolytic cleavage of the biopolymer thereby reducing the weight average molecular weight of the hyaluronic acid with time.

In some embodiments, the heat treated, filter sterilized, high salt, hyaluronic acid solution is used to prepare pharmaceutical formulations including those used in ophthalmic applications as well as in the treatment of osteoarthritis. Accordingly, the sterile filtered, high salt hyaluronic acid solution can be mixed with a pre-sterilized aqueous solution comprising other pharmaceutical formulation components including buffer components, e.g., boric acid and sodium borate. In the case of an ophthalmic formulation, the pH is adjusted from 6.4 to 7.2. By dividing the aqueous formulation into at least two separate parts or phases of commercial processing, the volume of the formulation that requires filter sterilization is significantly reduced. In many instances, the sterilized high salt, hyaluronic acid solution can be diluted by a factor of at least 10 to provide the desired concentration of hyaluronic acid in the pharmaceutical formulation; thereby less than one-tenth of the formulation would require filter sterilization. In another instance, the sterilized high salt, hyaluronic acid solution can be diluted by a factor of at least 5. Depending upon the remaining components in the pharmaceutical formulation the majority volume portion of the formulation can be heat sterilized, e.g., autoclaved, or this portion can also be filter sterilized (assuming, of course, the major volume of the formulation can be filtered with high efficiency).

Traditionally, a sterilizing filter medium is one that, when challenged with test organism *Brevundimonas diminuta* (*B. diminuta*) at a minimum concentration of $10^7$ colony forming units (CFU)/cm$^2$ produces a sterile effluent. The filter medium does play a role in the filtration flow rate (liters/min) for a given high salt, hyaluronic acid solution. A number of filter mediums are available for use in sterilizing filters. These include polyvinylidene fluoride (PVDF), polytetrafluoroethylene (PTFE) and polyethersulfone (PES). The filter membrane is then assembled into a cartridge. For example, Durapore® hydrophobic membrane cartridges are sterilizing-grade filters that provide sterility assurance, high flow rates and high throughput with minimal differential pressure. They are used for the filtration of liquids in small and large volume systems. Durapore® 0.22 μm hydrophobic polyvinylidene fluoride (PVDF) membrane reliably eliminates contaminants and microorganisms in sterilizing applications. The material of construction for the supporting filter structure (e.g., cage, core, endcaps and adapters) is usually polypropylene or a polysulfone.

In another embodiment, a process for sterilizing a solution comprising hyaluronic acid includes preparing an aqueous high salt, hyaluronic acid solution. The hyaluronic acid would have a weight average molecular weight from 0.6 MDa to 2.2 MDa, and a concentration of hyaluronic acid from 0.08% to 0.5% by weight. The hyaluronic solution will have an ionic strength equivalent to an aqueous concentration of sodium chloride from 4% to 18%. The relatively high ionic strength of the solution is provided by the addition of one or more ionic salts, e.g., sodium chloride or sodium borate. The high salt, hyaluronic acid solution is subjected to a heat treatment at a temperature from 50° C. to 75° C. for at least 1 hour and not longer than 18 hours. The heat treated solution is then filtered through a sterilization filter medium as described above. Again, to facilitate the dissolution of the hyaluronic acid in the water, the hyaluronic acid is preferably dry blended with the salt, e.g., NaCl. The dry blended salt/hyaluronic acid mixture is then slowly added to the water with agitation.

In another embodiment, the heat treatment of the high salt, hyaluronic acid solution comprises 0.1% to 0.4% by weight of hyaluronic acid, and 8% to 16% by weight of sodium chloride. The solution is then subjected to a heat treatment as described. Again, with a higher the maintenance temperature shorter maintenance times are needed. For example, if the aqueous high salt, hyaluronic acid solution aqueous high salt is maintained at a temperature from 55° C. to 65° C., a maintenance time of at least 2 hour and not longer that 8 hours is recommended.

The described filter sterilization processes for aqueous solutions containing hyaluronic acid can be used to prepare a sterilized aqueous solution comprising: 0.04% to 0.8% by weight hyaluronic acid with a weight average molecular weight from 0.6 MDa to 3.6 MDa. The aqueous solution will have an ionic strength equivalent to an aqueous concentration of sodium chloride from 4% to 18% by weight of sodium chloride and the solution is filter sterilized.

In one embodiment, the filter sterilized, high salt hyaluronic acid solution will have an ionic strength equivalent of approximately 25 g to 60 g of sodium chloride, for every one gram of hyaluronic acid in one liter of solution. For example, a 0.1 wt. % hyaluronic acid solution will include an ionic strength equivalent of approximately 25 g to 60 g of sodium chloride. Likewise, a 0.2 wt. % hyaluronic acid solution will include an ionic strength equivalent of approximately 50 g to 120 g of sodium chloride. A 0.3 wt. % hyaluronic acid solution will include an ionic strength equivalent of approximately 75 g to 180 g of sodium chloride.

In another embodiment, the described sterile filtration process can be used to prepare commercial-scale, production batch quantities of a contact lens care solution. The process would be similar to that described above with the exception that the final formulation would also include components suitable for a contact lens care solution. Some of these components as for hyaluronic acid may be more suitable for sterile filtration while others can likely be heat sterilized. Production batches having a final total solution volume from 5,000 L to 40,000 L can be prepared.

Again, one can begin with preparing an aqueous high salt, hyaluronic acid solution. The hyaluronic acid would have a weight average molecular weight from 0.6 MDa to 3.6 MDa, and a concentration of hyaluronic acid from 0.04% to 0.8% by weight. The hyaluronic solution will have an ionic strength equivalent to an aqueous concentration of sodium chloride from 3% to 30%. The relatively high ionic strength of the solution is provided by the addition of one or more ionic salts, e.g., sodium chloride or sodium borate. The high salt, hyaluronic acid solution is subjected to a heat treatment at a temperature from 55° C. to 75° C. for at least 1 hour and not longer than 12 hours. The heat treated solution is then filtered through a sterilization filter medium as described above.

The sterilized high salt, hyaluronic acid solution is then combined with a second aqueous solution that could contain most or all of the remaining components of the contact lens care solution, e.g., buffer components, one or more surfactants, one or more chelating agents and one or more antimicrobial components. Again, by combining the two aqueous solutions the sterilized high salt, hyaluronic acid solution is diluted by a factor of at least 5, or in some instances by a factor of at least 10.

As stated, the lens care solutions will also include one or more antimicrobial components selected from quarternary ammonium compounds (including small molecules) and polymers and low and high molecular weight biguanides. For example, biguanides include the free bases or salts of alexidine, chlorhexidine, hexamethylene biguanides and their polymers, and combinations thereof. In a preferred embodiment, the lens care solutions will include a polymeric biguanide known as poly(hexamethylene biguanide) (PHMB or PAPB) commercially available from Zeneca, Wilmington, Del. under the trademark Cosmocil™ CQ. The PHMB is present in the lens care solutions from 0.2 ppm to 5 ppm or from 0.5 ppm to 2 ppm.

One of the more common quaternary ammonium compounds is α-[4-tris(2-hydroxyethyl)-ammonium chloride-2-butenyl]poly[1-dimethyl ammonium chloride-2-butenyl]-ω-tris(2-hydroxyethyl) ammonium chloride, also referred to in the art as polyquaternium-1. Quaternary ammonium compounds are generally referred to in the art as "polyquaternium" disinfectants, and are identified by a particular number following the designation such as polyquaternium-1, polyquaternium-10 or polyquaternium-42. Polyquaternium-1 is present in the lens care solutions from 0.5 ppm to 3 ppm. Interestingly, attempts to increase the concentration of polyquaternium-1 beyond 3 ppm in the solutions results in the formation of a precipitate. The precipitate is believed to be the complexation product of hyaluronic acid and polyquaternium-1.

One of the more preferred combination of two antimicrobial components includes a mixture of PHMB at a concentration of from 0.5 ppm to 1.5 ppm and polyquaternium-1 at a concentration of from 0.5 ppm to 1.5 ppm. In such a formulation, the hyaluronic acid is present from 0.002 wt. % to 0.04 wt. %.

The contact lens care solution could also include 0.01 wt. % to 1 wt. % of an amphoteric surfactant of general formula I. Certain sulfobetaines of general formula I are more preferred than others. For example, sulfobetaine 3-10 wherein $R^1$ is a straight, saturated alkyl with ten (10) carbons, $R^2$ and $R^3$ are each methyl and $R^4$ is —$CH_2CH_2CH_2$— (three carbons, (3)). Other sulfobetaines that can be used in the ophthalmic compositions include the corresponding sulfobetaine 3-08

($R^1$ is a is a straight, saturated alkyl with eight carbons), sulfobetaine 3-12 ($R^1$ is a is a straight, saturated alkyl with twelve carbons), sulfobetaine 3-14 ($R^1$ is a is a straight, saturated alkyl with fourteen carbons) and sulfobetaine 3-16 ($R^1$ is a is a straight, saturated alkyl with sixteen carbons). Accordingly, some of the more preferred the ophthalmic composition will include a sulfobetaine of general formula I wherein $R^1$ is a $C_8$-$C_{16}$alkyl and $R^2$ and $R^3$ is methyl, and $R^4$ is —$CH_2CH_2CH_2$—.

I

Other components that can be included in a contact lens care solution are described in co-pending U.S. patent application Ser. No. 12/203,384 filed Sep. 3, 2008.

In one embodiment, aqueous solutions of sulfobetaine of general formula I, the PHMB and the polyquaternium-1 are prepared, and passed through a sterilization filter similar to a filter medium used to process the high salt, hyaluronic acid solution. Each of the filter sterilized solutions is then added to a common mixing tank.

EXAMPLE 12

A commercial scale, production batch of a contact lens, multi-purpose cleaning and disinfecting solution is prepared as four separate phases (aqueous solutions) and combined in a main mixing tank.

Phase 1. Into an appropriate size 316 stainless steel jacketed pressure vessel, equipped with agitation, add sufficient purified water to achieve maximum agitation. The phase 1 water volume should be about 60-96% of the total batch volume. Heat the water to achieve and/or maintain water temperature of not less then 70° C. Initiate agitation and maintain throughout the entire processing of the batch. In the order listed, add and dissolve the batch quantities of the following: edetate disodium, boric acid, sodium borate and poloxamine 1107. Mix the solution for not less than twenty minutes to ensure complete dissolution of the poloxamine 1107. Withdraw a solution sample and determine the pH. If necessary, adjust the pH to 7.3-7.7 with 1N NaOH or 1N HCl. Seal the reactor and heat sterilize the Phase 1 solution at 121-124° C. for 30-45 minutes using a validated cycle, and referring to General Procedure for Solutions Sterilized by Steam Under Pressure, for process and documentation requirements. Upon completion of the sterilization period, cool the phase 1 solution to less than 40° C.

Phase II. Phase II is an aqueous mixture of purified water, 0.26 wt. % hyaluronic acid and 13 wt. % sodium chloride. Combine and dry blend the batch quantities of hyaluronic acid and sodium chloride. While mixing an appropriate amount of water, slowly pour the dry-blended mixture of NaCl/hyaluronic acid into the mix tank. Mix the NaCl/hyaluronic acid solution while maintaining a 65-75° C. temperature range until the hyaluronic acid is completely dissolved. Visually examine the solution, slowing the mixer if necessary, to visually examine for any suspended hyaluronic acid.

Once the hyaluronic acid is completely dissolved, cool the solution to 50-55° C. Filter the NaCl/hyaluronic acid solution through sterilized Millipore CVGL filter(s) into the Phase I compounding tank. Differential pressure should not exceed 30 psi.

Phase III. To a suitable pressure vessel equipped with agitation, add 0.50%-4.95% the total batch weight of purified water at a temperature of less than 40° C. and a batch quantity of sulfobetaine powder to make a 0.05 wt. %-10.0 wt. % solution. Mix the solution for a minimum of twenty minutes. Aseptically filter the sulfobetaine solution into the Phase 1 solution through a sterile 0.22 μm Millipore filter (different filter assembly than used in the Phase II transfer). Mix the Phase I solution for not less than ten minutes.

Phase IV. To a suitable pressure vessel equipped with agitation, add 0.078%-1.98% of the total batch weight of cool (less than 40° C.) water plus the batch quantities of poly (hexamethylene biguanide) and polyquaternium-1 to make a 0.03%-1.00% solution. Mix the solution for a minimum of ten minutes. Aseptically filter the PHMB/PQ-1 solution into the Phase I solution through a sterile Millipore 0.22 μm filter.

EXAMPLE 13

A contact lens rewet eye drop formulation is prepared as follows. An aqueous, high salt, hyaluronate solution containing 3.0 wt. % boric acid NF, 2.1 wt. % NaCl USP, 0.7 wt. % KCl USP and 0.5 wt. % hyaluronic acid (average molecular weight of about 0.8 MDa) is prepared. A dry blended mixture of the HA and NaCl are slowly added over 5 min to heat distilled water maintained at about 68° C. in a stainless container with agitation. The HA appears fully dissolved after about 100 min. The solution is cooled to about 55° C. in about 8 min and maintained at about 55° C. for not less than 3 hours. The KCl and boric acid are added to the cooled, heat treated HA solution and the solution agitated for 10 min. The solution is sterile filtered by passing the solution through a PVDF 0.22 μm filter medium at a temperature of 55° C. Separately, a second sterilized, aqueous solution containing 1.75 wt. % sodium borate decahydrate. 0.03 wt. % calcium chloride dehydrate USP, 0.03 wt. % magnesium chloride hexahydrate and 0.025 wt. % of stabilized oxy-chloride complex (purite) is prepared. This second salt solution can be sterilized by using a conventional heat sterilization process. Alternatively, this solution can be sterile filtered using the same filter used in preparing the HA solution. Following sterilization of the second salt solution, the second solution is combined with the heat treated, high salt, hyaluronate solution at a volume ratio of 4:1, respectively. The final ophthalmic formulation, which can be used as a contact lens rewet eye drop formulation, is provided in Table 7.

TABLE 7

Contact lens rewet eyedrops

| Component | wt. % |
| --- | --- |
| sodium hyaluronate | 0.1 |
| sodium chloride | 0.42 |
| potassium chloride | 0.14 |
| boric acid | 0.6 |
| sodium borate | 0.035 |
| calcium chloride | 0.006 |
| magnesium chloride | 0.006 |
| stabilixed oxy-chloride (purite) | 0.005 |

We claim:
1. A process for sterilizing a solution, the process comprising:

providing an aqueous solution of hyaluronic acid having a weight average molecular weight from 0.6 MDa to 3.6 MDa, and the concentration of the hyaluronic acid is from 0.04% to 0.8% by weight; wherein the aqueous solution has an ionic strength equivalent to an aqueous concentration of sodium chloride from 3% to 30% by weight to provide a high salt, hyaluronic acid solution;

maintaining the aqueous high salt, hyaluronic acid solution at a temperature from 40° C. to 80° C. for at least 1 hour and not longer than six days; and filtering the heated, high salt, hyaluronic acid solution through a sterilization filter medium, wherein the filter medium has an average pore size of 0.25 μm or less to provide a sterilized high salt, hyaluronic acid solution.

2. The process of claim 1 wherein the hyaluronic acid has a weight average molecular weight from 0.8 MDa to 2.2 MDa.

3. The process of claim 1 wherein the concentration of the hyaluronic acid is from 0.1% to 0.5% by weight.

4. The process of claim 1 wherein providing the high salt, hyaluronic acid solution comprises combining and mixing an appropriate dry weight of salt and hyaluronic acid to from a dry blend of the salt and hyaluronic acid, and adding the dry blend to an appropriate amount of purified water.

5. The process of claim 4 wherein the purified water is pre-heated to a temperature from 40° C. to 70° C.

6. The process of claim 1 wherein the maintaining of the aqueous high salt, hyaluronic acid solution aqueous high salt comprises maintaining at a temperature from 50° C. to 65° C. for at least 1 hour and not longer that 12 hours.

7. The process of claim 1 further comprising combining the sterilized high salt, hyaluronic acid solution with an aqueous solution comprising buffer components and adjusting the pH from 6.4 to 7.2, and by the combining of the two aqueous solutions the sterilized high salt, hyaluronic acid solution is diluted by a factor of at least 10.

8. The process of claim 1 wherein the sterilized high salt, hyaluronic acid solution has a pH of 6.4 to 7.2.

9. The process of claim 7 wherein the buffer components comprise boric acid and sodium borate.

10. The process of claim 1 wherein the sterilized high salt, hyaluronic acid solution has a concentration of the hyaluronic acid from 0.15% to 0.6% by weight, and additionally contains sodium chloride at a concentration of from 4% to 16% by weight.

11. The process of claim 1 wherein the sterilization filter medium is a polyvinylidene fluoride filter cartridge.

12. A process for sterilizing a solution comprising hyaluronic acid, the process comprising:

providing an aqueous solution of hyaluronic acid with a weight average molecular weight from 0.6 MDa to 2.2 MDa, and the concentration of the hyaluronic acid is from 0.08% to 0.5% by weight; wherein the aqueous solution has an ionic strength equivalent to an aqueous concentration of sodium chloride from 4% to 18% by weight to provide a high salt, hyaluronic acid solution;

maintaining the aqueous high salt, hyaluronic acid solution at a temperature from 50° C. to 75° C. for at least 1 hour and not longer than 18 hours; and filtering the heated, high salt, hyaluronic acid solution through a sterilization filter medium, wherein the filter medium has an average pore size of 0.25 μm or less to provide a sterilized high salt, hyaluronic acid solution.

13. The process of claim 12 wherein tile sterilized high salt, hyaluronic acid solution has a concentration of the hyaluronic acid from 0.1% to 0.4% by weight, and additionally contains sodium chloride at a concentration of from 8% to 16% by weight.

14. The process of claim 12 wherein providing the high salt, hyaluronic acid solution comprises combining and mixing an appropriate dry weight of salt and hyaluronic acid to from a dry blend of the salt and hyaluronic acid, and adding the dry blend to an appropriate amount of purified water.

15. The process of claim 12 further comprising combining the sterilized high salt, hyaluronic acid solution with an aqueous solution comprising buffer components selected from the group consisting of boric acid, sodium borate, sodium dihydrogen phosphate and adjusting the pH from 6.4 to 7.2, and by the combining of the two aqueous solutions the sterilized high salt, hyaluronic acid solution is diluted by a factor of at least 5.

16. The process of claim 15 wherein the combined aqueous solutions further comprise stabilized chlorine in a preservative effective amount.

17. The process of claim 12 wherein the sterilization filter medium is a polyvinylidene fluoride filter cartridge.

18. A process of preparing a production batch of a contact lens care solution, the process comprising:

providing an aqueous solution of hyaluronic acid with a weight average molecular weight from 0.6 MDa to 3.6 MDa, and the concentration of the hyaluronic acid is from 0.04% to 0.8% by weight; wherein the aqueous solution has an ionic strength equivalent to an aqueous concentration of sodium chloride from 2% to 30% by weight to provide a high salt, hyaluronic acid solution;

maintaining the aqueous high salt, hyaluronic acid solution at a temperature from 55° C. to 75° C. for at least 1 hour and not longer than 12 hours;

filtering the heated, high salt, hyaluronic acid solution through a sterilization filter medium, wherein the filter medium has an average pore size of 0.25 μm or less to provide a sterilized high salt, hyaluronic acid solution;

combining the sterilized high salt, hyaluronic acid solution with an aqueous solution comprising buffer components and adjusting the pH from 6.4 to 7.2, and by the combining of the two aqueous solutions the sterilized high salt, hyaluronic acid solution is diluted by a factor of at least 10.

19. The process of claim 18 wherein the combined aqueous solutions further comprise poly(hexamethylene biguanide), which is present from 0.5 ppm to 2.0 ppm.

20. The process of claim 19 wherein the combined aqueous solutions further comprise α-[4-tris(2-hydroxyethyl)-ammonium chloride-2-butenyl]poly[1-dimethyl ammonium chloride-2-butenyl]-ω-tris(2-hydroxyethyl)ammonium chloride, which is present from 0.5 ppm to 3 ppm.

21. The process of claim 18 wherein the production batch has a final total solution volume from 5,000 L to 40,000 L.

* * * * *